US00PP23449P2

(12) United States Plant Patent
Barends

(10) Patent No.: US PP23,449 P2
(45) Date of Patent: Mar. 5, 2013

(54) ***OSTEOSPERMUM* PLANT NAMED 'FIDOSTNANOYEL'**

(50) Latin Name: *Osteospermum ecklonis*
Varietal Denomination: Fidostnanoyel

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 14 days.

(21) Appl. No.: 13/200,153

(22) Filed: Sep. 19, 2011

(51) Int. Cl.
*A01H 5/00* (2006.01)

(52) U.S. Cl. ..... Plt./360

(58) Field of Classification Search ..... Plt./360
See application file for complete search history.

*Primary Examiner* — Howard Locker
(74) *Attorney, Agent, or Firm* — C. A. Whealy

(57) ABSTRACT

A new and distinct cultivar of *Osteospermum* plant named 'Fidostnanoyel', characterized by its compact and mounding plant habit; freely branching growth habit; early and freely flowering habit; daisy-type inflorescences with yellow-colored ray florets; and good garden performance.

1 Drawing Sheet

Botanical designation: *Osteospermum ecklonis.*
Cultivar denomination: 'FIDOSTNANOYEL'.

BACKGROUND OF THE INVENTION

The present invention relates to a new and distinct cultivar of *Osteospermum* plant, botanically known as *Osteospermum ecklonis*, and hereinafter referred to by the name 'Fidostnanoyel'.

The new *Osteospermum* plant is a product of a planned breeding program conducted by the Inventor in De Lier, The Netherlands. The objective of the program is to create and develop new compact *Osteospermum* plants that are freely branching, early and freely flowering and have attractive inflorescence coloration.

The new *Osteospermum* plant originated from a cross-pollination by the Inventor in May, 2005 of a proprietary selection of *Osteospermum ecklonis* identified as code number O 45707, not patented, as the female, or seed, parent with a proprietary selection of *Osteospermum ecklonis* identified as code number O 67238, not patented, as the male, or pollen, parent. The new *Osteospermum* plant was discovered and selected by the Inventor as a single flowering plant within the progeny of the stated cross-pollination in a controlled greenhouse environment in De Lier, The Netherlands in October, 2005.

Asexual reproduction of the new *Osteospermum* plant by terminal cuttings in a controlled greenhouse environment in De Lier, The Netherlands since Nov. 1, 2005, has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fidostnanoyel'. These characteristics in combination distinguish 'Fidostnanoyel' as a new and distinct *Osteospermum* plant:

1. Compact and mounding plant habit.
2. Freely branching growth habit.
3. Early and freely flowering habit.
4. Daisy-type inflorescences with yellow-colored ray florets.
5. Good garden performance.

Plants of the new *Osteospermum* differ from plants of the female parent selection primarily in ray floret color as plants of the female parent selection have white-colored ray florets.

Plants of the new *Osteospermum* differ from plants of the male parent selection primarily in flowering habit as plants of the new *Osteospermum* flower earlier than plants of the male parent selection.

Plants of the new *Osteospermum* can be compared to plants of the *Osteospermum* 'Margarita Yellow', not patented. In side-by-side comparisons conducted in De Lier, The Netherlands, plants of the new *Osteospermum* differed primarily from plants of 'Margarita Yellow' in the following characteristics:

1. Plants of the new *Osteospermum* were more compact than plants of 'Margarita Yellow'.
2. Plants of the new *Osteospermum* flowered earlier than plants of 'Margarita Yellow'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant. The photograph comprises a side perspective view of typical flowering plants of 'Fidostnanoyel' grown in container trays.

DETAILED BOTANICAL DESCRIPTION

The aforementioned photograph, following observations and measurements describe plants grown during the spring in container trays, each tray with six 9-cm compartments, in a glass-covered greenhouse in De Lier, The Netherlands and under environmental conditions and cultural practices which approximate those generally used in commercial *Osteospermum* production. During the production of the plants, day temperatures ranged from 17° C. to 35° C. and night temperatures ranged from 15° C. to 25° C. Plants were twelve weeks old when the photograph and description were taken. In the following description, color references are made to The Royal Horticultural Society Colour Chart, 2007 Edition, except where general terms of ordinary dictionary significance are used.

Botanical classification: *Osteospermum ecklonis* 'Fidostnanoyel'.

Parentage:

*Female, or seed, parent*.—Proprietary selection of *Osteospermum ecklonis* identified as code number O 45707, not patented.

*Male, or pollen, parent*.—Proprietary selection of *Osteospermum ecklonis* identified as code number O 67238, not patented.

Propagation:

*Type*.—Terminal vegetative cuttings.

*Time to initiate roots, summer*.—About six days at 22° C.

*Time to initiate roots, winter*.—About one week at 22° C.

*Time to produce a rooted cutting, summer*.—About twelve days at 22° C. to 30° C.

*Time to produce a rooted cutting, winter*.—About two weeks at 20° C. to 25° C.

*Root description*.—Medium in thickness, fibrous; whitish grey in color.

*Rooting habit*.—Moderately freely branching; medium density.

Plant description:

*Plant and growth habit*.—Compact and mounding plant habit; relatively short internodes, dense and bushy growth habit; moderately vigorous growth habit.

*Plant height*.—About 11 cm.

*Plant diameter*.—About 11 cm.

*Lateral branches*.—Quantity per plant: Freely branching habit with about twelve lateral branches developing per plant; pinching is not required, however pinched plants will be larger than non-pinched plants. Length: About 7 cm to 8 cm. Diameter: About 1 mm to 3 mm. Internode length: About 0.5 cm to 3.5 cm. Strength: Strong, sturdy. Aspect: About 20° to 45° from vertical. Texture: Sparsely pubescent. Color: Close to 144C.

*Foliage description*.—Arrangement: Alternate, simple; sessile. Length: About 4.5 cm. Width: About 2 cm. Shape: Elliptic. Apex: Acute. Base: Attenuate. Margin: Lobed; serrate. Texture, upper surface: Smooth, glabrous. Texture, lower surface: Sparsely pubescent. Venation pattern: Pinnate. Color: Developing leaves, upper surface: Close to 137B. Developing leaves, lower surface: Close to 146A. Fully expanded leaves, upper surface: Close to N137B; venation, close to 145C. Fully expanded leaves, lower surface: Close to 146B; venation, close to 145B.

Inflorescence description:

*Appearance*.—Daisy-type inflorescence form with elliptic to slightly obovate-shaped ray florets; inflorescences positioned beyond the foliar plane on moderately strong peduncles; inflorescences terminal and axillary; inflorescences face upright; ray and disc florets developing acropetally on a capitulum.

*Flowering habit*.—Freely flowering habit; about 20 to 30 inflorescences developing per plant.

*Fragrance*.—None detected.

*Flowering response*.—In The Netherlands, plants of the new *Osteospermum* flower continuously from spring to frost in the autumn; early flowering habit, plants begin flowering about six weeks after planting.

*Inflorescence longevity*.—At temperatures of 14° C. to 20° C., inflorescences last about 2.5 weeks on the plant; inflorescences persistent.

*Inflorescence bud*.—Height: About 1.8 cm. Diameter: About 1.2 cm. Shape: Globular to ovoid. Color: Close to 137A.

*Inflorescence size*.—Diameter: About 5 cm. Depth (height): About 1 cm. Disc diameter: About 1 cm. Receptacle diameter: About 7 mm. Receptacle height: About 4 mm. Receptacle color: Close to 146A.

*Ray florets*.—Length: About 3 cm. Width: About 8 mm. Shape: Elliptic to slightly obovate. Apex: Rounded to slightly obtuse. Base: Attenuate. Margin: Entire. Texture: Smooth, glabrous; satiny. Number of ray florets per inflorescence and arrangement: About 13 to 15 in a single whorl. Color: When opening, upper surface: Close to 7C; towards the apex, close to 7A. When opening, lower surface: Longitudinal stripes, close to 7D, 177A and 174A. Fully opened, upper surface: Close to 13D; towards the base, close to NN155D; color becoming closer to 159C with development. Fully opened, lower surface: Longitudinal stripes, close to 174A and 174C; color becoming closer to 13A, 177A and 174A with development.

*Disc florets*.—Shape: Tubular; apex dentate, five-pointed. Length: About 7 mm. Diameter: About 1 mm to 1.5 mm. Number of disc florets per inflorescence: About 20 to 22. Color, immature and mature: Apex: Close to 91A. Mid-section: Close to NN155D. Base: Close to NN155D.

*Phyllaries*.—Quantity per inflorescence: About 19 to 20 in 1.5 whorls. Length: About 8 mm. Width: About 1 mm to 3 mm. Shape: Lanceolate. Apex: Acuminate. Base: Truncate. Margin: Entire. Texture, upper and lower surfaces: Sparsely pubescent. Color, upper surface: Close to 146A. Color, lower surface: Close to 138A.

*Peduncles*.—Length, terminal peduncles: About 5 cm. Length, axillary peduncles: About 7 cm. Diameter: About 1.5 mm. Strength: Moderately strong. Aspect: Mostly upright. Texture: Pubescent. Color: Close to 144A.

*Reproductive organs*.—Androecium: Present on disc florets only. Filament length: About 3 mm. Filament color: Close to NN155D. Anther shape: Lanceolate. Anther length: About 2 mm. Anther color: Close to N77A. Pollen amount: Moderate. Pollen color: Close to 15B. Gynoecium: Present on both ray and disc florets. Pistil length: About 5 mm. Stigma shape: Biparted. Stigma color: Close to 79A. Style length: About 4 mm. Style color: Close to NN155D. Ovary color: Close to NN155D.

*Seeds and fruits*.—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about 4° C. to about 35° C.

It is claimed:

1. A new and distinct *Osteospermum* plant named 'Fidostnanoyel' as illustrated and described.

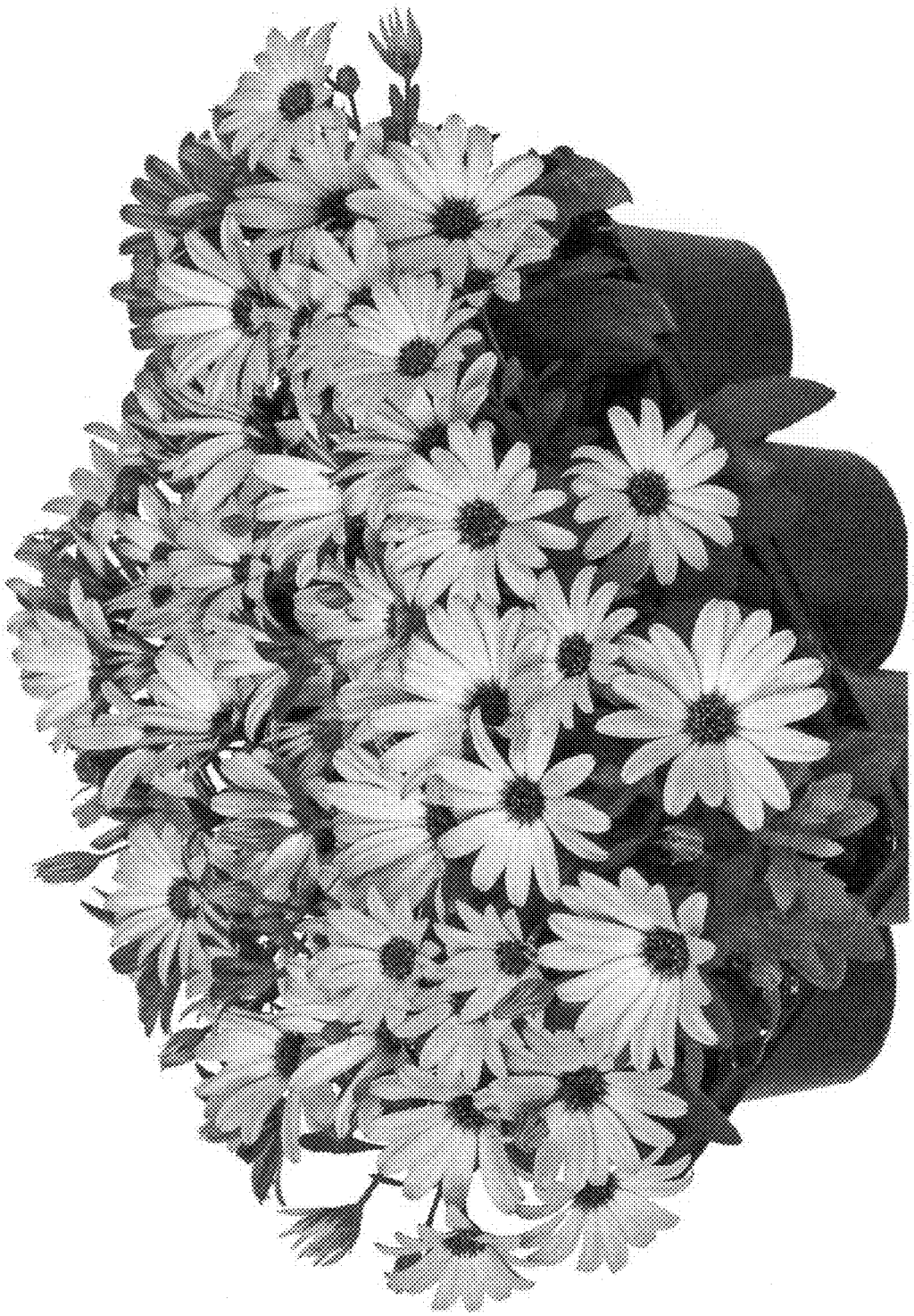

* * * * *